US008685468B2

(12) United States Patent
Lo et al.

(10) Patent No.: US 8,685,468 B2
(45) Date of Patent: Apr. 1, 2014

(54) SURGICAL ADJUVANT COMPOSITION AND ASSOCIATED METHODS OF USE

(76) Inventors: Ian K. Y. Lo, Calgary (CA); Paul Sciore, Calgary (CA); Ken Muldrew, Calgary (CA)

( * ) Notice: Subject to any disclaimer, the term of this patent is extended or adjusted under 35 U.S.C. 154(b) by 391 days.

(21) Appl. No.: 12/791,046

(22) Filed: Jun. 1, 2010

(65) Prior Publication Data
US 2011/0293749 A1 Dec. 1, 2011

(51) Int. Cl.
*A01N 59/00* (2006.01)
*A61K 33/00* (2006.01)

(52) U.S. Cl.
USPC .......................................................... 424/722

(58) Field of Classification Search
USPC .......................................................... 424/722
See application file for complete search history.

(56) References Cited

U.S. PATENT DOCUMENTS

2002/0028798 A1* 3/2002 Demopulos et al. ....... 514/210.2

FOREIGN PATENT DOCUMENTS

WO WO 0035420 A2 * 6/2000

OTHER PUBLICATIONS

Chahine et al., Effect of Dynamic Loading on the Transport of Solutes into Agarose Hydrogels, Biophysical J 97: 968-975 (2009).*
Lee et al., Surfactant-induced sealing of electropermeabilized skeletal muscle membranes in vivo, Proc Natl Acad Sci USA 89: 4524-4528 (1992).*
WO 2011/151731 International Search Report, 2011.
WO 2011/151731 Written Opinion of the International Searching Authority, 2011.
Sakuma N., et al., "Both HDL3 and HDL2 Exert a Powerful Anti-Oxidative and Protective Effect Against Acceleration of Oxidative Modification of LDL by Absorbic Acid", Journal of Nutritional Science and Vitaminology, vol. 51, No. 2, pp. 75-79, 2005.
Memon S. and Pratten M.K., "Developmental toxicity of ethanol in chick heart in ovo and in micromass culture can be prevented by addition of vitamin C and folic acid", Reproductive Toxicology, vol. 28, pp. 262-269, 2009.
Gupta, Y., et al., "Transferrin-conjugated solid lipid nanoparticles for enhanced delivery of quinine dihydrochloride to the brain", Journal of Pharmacy and Pharmacology, vol. 59, pp. 935-940, Jul. 2007.
Lo, I.K.Y., et al., "Local Anesthetics Induce Chondrocyte Death in Bovine Articular Cartilage Disks in a Dose- and Duration-Dependent Manner", Arthroscopy: The Journal of Arthroscopic and Related Surgery, vol. 25, pp. 707-715, Jul. 2009.

* cited by examiner

*Primary Examiner* — Abigail Fisher
*Assistant Examiner* — Thor Nielsen
(74) *Attorney, Agent, or Firm* — Edwards Wildman Palmer LLP; Bryan D. Zerhusen; Gabriel J. McCool

(57) ABSTRACT

Disclosed herein are surgical adjuvant compositions for ameliorating tissue and cellular necrosis and/or apoptosis. In addition, surgical methods are described which include the use of the adjuvant of the composition to reduce tissue and cellular necrosis and/or apoptosis.

26 Claims, 7 Drawing Sheets

SURGICAL ADJUVANT COMPOSITION AND ASSOCIATED METHODS OF USE

FIELD OF THE INVENTION

The present invention relates to a surgical adjuvant composition that provides for reduced tissue and cellular necrosis and/or apoptosis. The composition is particularly useful, for example, for use in arthroscopic surgical procedures and other minimally invasive endoscopic procedures where an irrigant is useful.

BACKGROUND

Arthroscopic joint surgery is one of the most commonly performed procedures in surgical practice and its use is steadily increasing. For example, more than 2 million arthroscopic procedures were performed in the United States in 2003, and that number is steadily increasing. In Canada, thousands of arthroscopic procedures are performed every year with some procedures being performed completely arthroscopically as opposed to traditional open approaches.

One major advantage of arthroscopic surgery is its minimal invasive fashion which limits surgical wounds, bleeding, and in particular, limits post-operative pain and recovery time. During arthroscopy, irrigating solutions are used to distend and flush the joint. Two of the most commonly used irrigating solutions are saline and Ringer's lactate. Despite the relative safety of their use intra-vascularly, the short and long term effects and relative safety of their use in other environments is unclear. Furthermore the prolonged bathing of articular tissue in these foreign environments is unclear. In fact, there is mounting evidence that commonly used fluids and drugs given intra-articularly may be detrimental to joint tissue viability.

For example, in an effort to improve post-operative pain control and limit systemic side effects, the use of intra-articular local anesthetics (e.g. bupivacaine, xylocaine, ropivicaine) has gained popularity. Local anesthetic use following arthroscopic surgery is routinely performed as a single dose intra-articular injection. Furthermore, to provide even longer term relief, continuous infusion of intra-articular local anesthetics is commonly performed for up to 48-72 hours.

However, a number of recent in vitro studies have demonstrated that local anesthetics are, in fact, highly toxic to articular tissues. For example, several studies have documented that exposure to local anesthetics decreased cellular viability of articular tissues in a dose and duration dependent manner. Additionally, many have reported acute chondrolysis (i.e. cartilage cell death and loss of tissue integrity) following prolonged intra-articular local anesthetic infiltration.

During the course of arthroscopic surgery, it is common to use electrical cauterization and, or mechanical drilling, burring, or grinding to effect changes to the tissue. These procedures generate excessive heat that can lead to collateral morbidity to the cells and tissues near the site of repair. In addition, the instruments used during an arthroscopic procedure can impact and cut the articular cartilage, insults that have been linked to chondrocyte death (Am J Sports Med 2009, 37: 2318-23).

Our studies have investigated the effects of irrigant fluids (e.g saline, ringers lactate) on tissue viability (FIG. 1, See Appendix). The effects of irrigant fluids on tissue viability has also been investigated. Studies using both in vitro and in vivo animal models, have demonstrated detrimental effects of non-physiologic fluids (e.g. normal saline, ringers lactate) on cartilage morphology, ultrastructure, metabolism, and biomechanics (J Bone Joint Surg Am 1983, June 65(5):629-3). Based on this data there is an ongoing need to develop a physiologic solution applicable to medical and veterinary surgical needs that can ameliorate the problem of tissue destruction resulting from the detrimental effects of non-physiologic surgical adjuvants and irrigants, as well as the collateral mechanical and thermal damage associated with surgical intervention.

SUMMARY

Presently described are surgical adjuvant/irrigant compositions that surprisingly and unexpectedly ameliorate or reduce tissue and cellular necrosis and/or apoptosis, and associated methods of use and manufacture. The compositions described herein can replace the irrigants normally or currently used in arthroscopy.

In one aspect, compositions are provided that are useful as surgical adjuvants or irrigants, for example, replacing the irrigant normally used in arthroscopy. For example, in certain embodiments the composition comprises a combination of isotonic phosphate buffered saline, high molecular weight dextran, ascorbate, transferrin, and the poloxamer surfactant P188. In another aspect, the surgical adjuvant composition of the invention further comprises an anesthetic, for example, a local anesthetic and/or epinephrine injected into the joint space during or following the procedure.

In another aspect, the invention provides compositions for use as a carrier or an additive to a surgical irrigant.

In another aspect, the invention provides methods of performing a surgical procedure using the composition of the invention. In certain embodiments, this aspect includes methods for performing arthroscopic surgical procedures using the composition of the invention. In another aspect, the invention provides carriers for drug delivery to the joint space, or the site of surgical intervention.

In another aspect, the invention provides compositions useful as a biological fluid replacement.

The preceding general areas of utility are given by way of example only and are not intended to be construed as limiting on the scope of the invention. Additional objects and advantages of the present invention will be appreciated by one of ordinary skill in the art in light of the instant claims, description, and examples. For example, the various aspects and embodiments of the invention may be utilized in numerous combinations, all of which are expressly contemplated by the present description. These additional advantages objects and embodiments are expressly included within the scope of the present invention.

BRIEF DESCRIPTION OF THE DRAWINGS

The accompanying drawings, which are incorporated into and form a part of the specification, illustrate several embodiments of the present invention and, together with the description, serve to explain the principles of the invention. The drawings are only for the purpose of illustrating an embodiment of the invention and are not to be construed as limiting the invention. Further objects, features and advantages of the invention will become apparent from the following detailed description taken in conjunction with the accompanying figures showing illustrative embodiments of the invention, in which.

Figure 1:
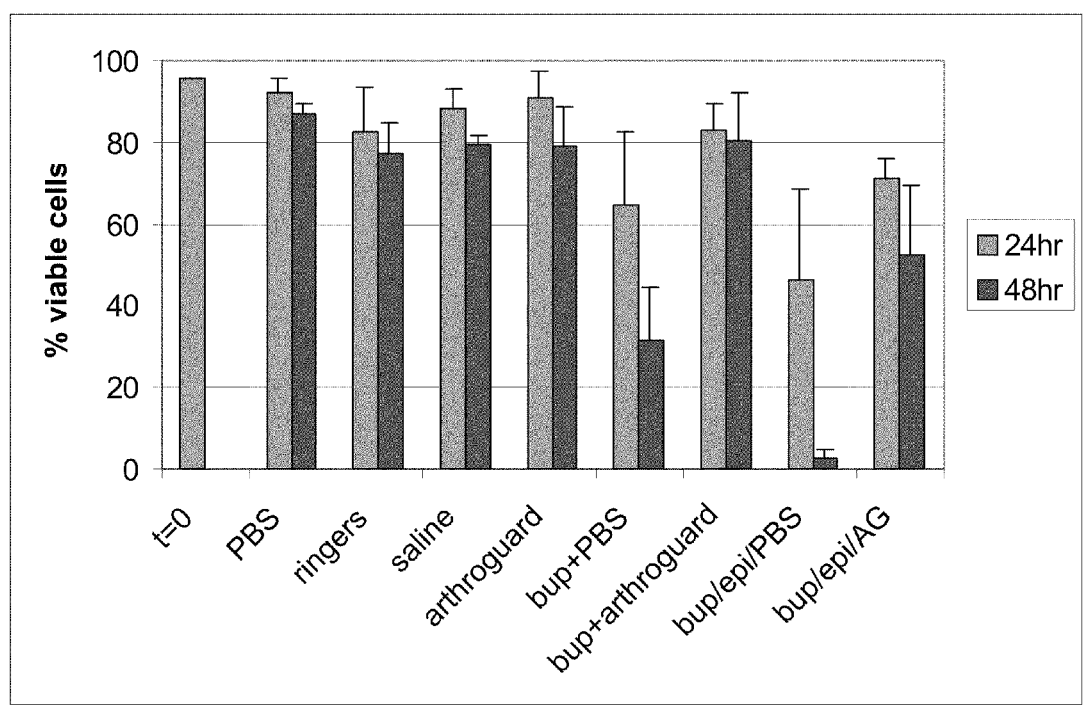
FIG. 1 shows the effects of the composition of the invention on cell viability compared to bathing solutions of saline, Ringer's Lactate, and phosphate buffered saline. Cell counts were taken at about 24 and about 48 hours in the absence and presence of anesthetic. T=0: initial viability; PBS: phosphate buffered saline; Ringers: Ringer's Lactate; bup: bupivacaine; epi: epinephrine; AG ("arthroguard") exemplary composition provided by the invention ("arthroguard"). Error bars show standard deviation.

As indicated above, the figures are provided for exemplary purposes only and are not to be construed as limiting. For example, as would be understood by those skilled in the art, any of the features described in the figures can be combined with any other embodiment or embodiments in any conceivable combination, all of which are contemplated by the inventors, and encompassed by the present claims.

DETAILED DESCRIPTION

The present invention relates to a surgical adjuvant/irrigant composition that surprisingly and unexpectedly ameliorates or reduces tissue and cellular necrosis and/or apoptosis.

The following is a detailed description of the invention provided to aid those skilled in the art in practicing the present invention. Those of ordinary skill in the art may make modifications and variations in the embodiments described herein without departing from the spirit or scope of the present invention. Unless otherwise defined, all technical and scientific terms used herein have the same meaning as commonly understood by one of ordinary skill in the art to which this invention belongs. The terminology used in the description of the invention herein is for describing particular embodiments only and is not intended to be limiting of the invention.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges which may independently be included in the smaller ranges is also encompassed within the invention, subject to any specifically excluded limit in the stated range. Where the stated range includes one or both of the limits, ranges excluding either both of those included limits are also included in the invention.

Although any methods and materials similar or equivalent to those described herein can also be used in the practice or testing of the present invention, the preferred methods and materials are now described. All publications mentioned herein are expressly incorporated herein by reference in their entirety to disclose and describe the methods and/or materials in connection with which the publications are cited.

It must be noted that as used herein and in the appended claims, the singular forms "a", "and", and "the" include plural references unless the context clearly dictates otherwise.

Unless defined otherwise, all technical and scientific terms used herein have the meaning commonly understood by a person skilled in the art to which this invention belongs. The following references, the entire disclosures of which are incorporated herein by reference, provide one of skill with a general definition of many of the terms used in this invention: Singleton et al., Dictionary of Microbiology and Molecular Biology ($2^{nd}$ ed. 1994); The Cambridge Dictionary of Science and Technology (Walker ed., 1988); The Glossary of Genetics, $5^{th}$ Ed., R. Rieger et al. (eds.), Springer Verlag (1991); and Hale & Marham, the Harper Collins Dictionary of Biology (1991). As used herein, the following terms may have meanings ascribed to them below, unless specified otherwise. However, it should be understood that other meanings that are known or understood by those having ordinary skill in the art are also possible, and within the scope of the present invention. All publications, patent applications, patents, and other references mentioned herein are incorporated by reference in their entirety. In the case of conflict, the present specification, including definitions, will control. In addition, the materials, methods, and examples are illustrative only and not intended to be limiting.

As described above, the use of saline as an irrigant may lead to chondrocyte necrosis and/or apoptosis in the superficial zone of articular cartilage. The present invention relates to the surprising discovery that irrigation of a surgical site using a solution comprising isotonic phosphate buffered saline in combination with at least one of a high molecular weight dextran, ascorbate, transferrin or poloxamer surfactant P188 reduces the necrosis and/or apoptosis in the superficial zone and elsewhere in the articular cartilage. Accordingly, the present invention provides a composition comprising isotonic phosphate buffered saline in combination with at least one of a high molecular weight dextran, ascorbate, transferrin or poloxamer surfactant P188. In another embodiment, the composition provided by the invention comprises isotonic phosphate buffered saline, and polyoxamer surfactant P188 in combination with at least one of a high molecular weight dextran, ascorbate, or transferrin. In another embodiment, the composition provided by the invention provides, comprises isotonic phosphate buffered saline, polyoxamer surfactant P188, a high molecular weight dextran, ascorbate, and transferrin. The compositions provided by the invention appear to function synergistically to promote the viability of cells when exposed to cytotoxic agents, including, for example, local anesthetics.

In addition, the use of local anaesthetics and/or epinephrine in the joint space has been shown to lead to chondrocyte necrosis and/or apoptosis. However, it has been surprisingly and unexpectedly discovered that irrigation of a surgical site using a solution comprising isotonic phosphate buffered saline, and at least one of poloxamer surfactant P188, high molecular weight dextran, ascorbate, transferring or a combination thereof, reduces the necrosis and/or apoptosis caused by local anesthetics and/or epinephrine. In certain embodiments, the solution comprises isotonic phosphate buffered saline, poloxamer surfactant P188, and at least one or more of a high molecular weight dextran, ascorbate, transferrin or a combination thereof.

In another aspect, the invention provides compositions for the delivery of an anesthetic, local or general. For example, the composition comprises isotonic phosphate buffered saline in combination with at least one of a high molecular weight dextran, ascorbate, transferrin or poloxamer surfactant P188 in combination with an anesthetic. Many anesthetics are known by those of skill in the art and can be used with the present invention. For example, in any of the embodiments described herein, the composition may contain morphine, fentanyl, gabapentin, Opioids, Alfentanil, Anileridine, Fentanyl, Phenoperidine. Remifentanil, Sufentanil, Neuroactive steroids Alfaxalone, Minaxolone, Droperidol, Etomidate, Fospropofol, gamma-Hydroxybutyric acid, Ketamine/Esketamine, Midazolam, Propanidid, or Propofol. anesthetic. In certain additional embodiments, the composition comprises a local anesthetic. Examples of local anesthetics that can be used with any of the embodiments described herein, include bupivacaine, xylocaine/lidocaine, ropivacaine, and combinations thereof. Accordingly, in another embodiment, the composition comprises isotonic phosphate buffered saline in combination with at least one of a high molecular weight dextran, ascorbate, transferrin or poloxamer surfactant P188 in combination with at least one of bupivacaine, xylocaine/lidocaine, ropivacaine, or a combination thereof.

In any of the embodiments described herein, the composition may further comprise an effective amount of epinephrine or other monoamine. Epinephrine, also known as adrenaline, is a hormone and neurotransmitter. When produced in the body it increases heart rate, contracts blood vessels and dilates air passages and participates in the fight-or-flight response of the sympathetic nervous system. It is a catecholamine, a monoamine produced only by the adrenal glands from the amino acids phenylalanine and tyrosine. Due to its vasoconstrictive effects, adrenaline is the drug of choice for treating anaphylaxis.

Although the precise mode of action of the irrigant remains to be fully understood, and without being limited to any particular theory, the individual components of the arthroguard solution are hypothesized to act both individually and collectively to prevent cell death due to exposure to anaesthetics and/or epinephrine. For example, phosphate buffered saline may provide a pH buffer as well as essential ions for osmotic balance. Dextran may provide a non-ionic osmoticum that may reduce or prevent swelling of the cells and/or tissue. Ascorbate is an antioxidant that may reduce or prevent lipid peroxidation, which can be a precursor to apoptosis. Transferrin binds any free ferrous ions which may otherwise react through the Fenton reaction to produce hydroxyl radicals that react non-specifically with lipids and other organic molecules, possibly initiating apoptosis. The poloxamer P188 may stabilize membrane pores and/or blebs that form in the initial stages of apoptosis and many types of necrosis.

In any of the embodiments encompassed herein, the concentrations of reagents may be within the following ranges: (i) dextran: from about 0.1 mg/mL to about 1000 mg/mL, (ii) P188: from about 0.1 mg/mL to about 100 mg/mL, (iii) ascorbate: from about 0.1 mM to about 100 mM, (iv) transferrin: from about $10^{-7}$ M to about $10^{-4}$ M.

Membrane stabilization may be an important intervention that halts and/or reverses the apoptotic progression allowing cells to recover from the injury that precipitated the cascade. Membrane stabilization may also allow the resealing of membrane pores that accompany many types of necrosis, preventing cell lysis that may be the endpoint of the necrotic process. Both apoptotic and necrotic cell death progressions may be initiated by singular events or multiple sub-lethal injuries, therefore these agents may act individually to prevent cell death in some circumstances but collectively in others. The synergistic effects of the reagents may not manifest themselves in all situations nevertheless they may still retain crucial importance for the effectiveness of the compositions provided by the invention.

In additional embodiments, compositions provided by the invention may comprise any pharmaceutically acceptable carriers or excipients, including sugars, sugar alcohols, such as lactose, sucrose, trehalose, mannitol and sorbitol; cellulose preparations such as maize starch, wheat starch, rice starch, potato starch, gelatin, gum tragacanth, methyl cellulose, hydroxypropylmethyl-cellulose, sodium carboxymethylcellulose; water, glycols, oils, alcohols, coloring agents, flavoring agents, preservatives, and/or polyvinylpyrrolidone (PVP); granulating agents; binding agents; cross-linked polyvinylpyrrolidone; agar; or alginic acid or a salt thereof such as sodium alginate.

In any of the embodiments described herein, the composition provided by the invention may be combined with one or more cell and/or tissue biocompatible solutions or cell/tissue media. For example, known biocompatible solutions or cell media include Ringer's solution, Ringer's Lactate, saline, balanced salt solutions, phosphate buffered saline, biopreservation solutions, Eurocollins solution, UW solution, Hank's buffered salt solution, Earl's balanced salt solution, Dulbecco's phosphate buffered saline or combinations thereof. Additional biocompatible solutions or cell/tissue media are known and may become known to those of skill in the art and their use in combination with the compositions of the invention are explicitly contemplated as being within the scope of the invention.

In another aspect, the invention provides a composition useful as a surgical adjuvant for the amelioration of tissue and/or cellular damage, for example, due to a surgical procedure. Accordingly, the present invention provides a surgical adjuvant composition comprising isotonic phosphate buffered saline in combination with at least one of a high molecular weight dextran, ascorbate, transferrin or poloxamer surfactant P188. In another embodiment, the invention provides a surgical adjuvant composition comprising isotonic phosphate buffered saline, and polyoxamer surfactant P188 in combination with at least one of a high molecular weight dextran, ascorbate, or transferrin. In another embodiment, the invention provides a surgical adjuvant composition comprising isotonic phosphate buffered saline, polyoxamer surfactant P188, a high molecular weight dextran, ascorbate, and transferrin.

The surgical adjuvant as described herein ameliorates and/or prevents tissue and/or cellular damage due to a surgical procedure, for example, an invasive or minimally invasive procedure (e.g., endoscopic, thoracoscopic or laparoscopic procedure). Therefore, in another aspect, the invention provides a method for ameliorating and/or preventing tissue and/or cellular damage due to an invasive or minimally invasive surgical procedure, wherein the composition ameliorates tissue or cellular damage. In an embodiment of this aspect, the method comprises the steps of administering to the patient an effective amount of the adjuvant as described herein at any point during the procedure. For example, the surgical adjuvant composition can be administered before, during, and/or after the surgical procedure. In still another embodiment, the surgical adjuvant composition is administered (i.e., perfused) continuously through or over the surgical site from prior to the procedure and continuing until some time after the conclusion of the procedure. Of course, the appropriate amount of adjuvant and/or rate of perfusion to be used in any instance can be readily determined by the skilled artisan in view of the present teachings and knowledge of those skilled in the art.

In another aspect, the composition provided by the invention may be used as a carrier and/or diluent for the delivery of one or more pharmaceutical or biologically beneficial and/or biologically active therapeutic agents. For example, in an exemplary embodiment, the carrier comprises an isotonic phosphate buffered saline, and at least one of poloxamer surfactant P188, high molecular weight dextran, ascorbate, transferrin or a combination thereof, in combination with at least one of, for example, a vitamin, coenzyme, herbal extract or other dietary supplement ingredient, saccharide, carbohydrate, glycan, proteoglycan, small molecule drug, antibody and/or antibody fragment, protein, peptide, or the like. In still another embodiment, the carrier comprises an isotonic phosphate buffered saline, a poloxamer surfactant P188, and at least one of a high molecular weight dextran, ascorbate, transferrin or a combination thereof, in combination with at least one of, for example, a vitamin, coenzyme, herbal extract or other dietary supplement ingredient, saccharide, carbohydrate, glycan, proteoglycan, small molecule drug, antibody and/or antibody fragment, protein, peptide, or the like.

Specific examples of biologically beneficial ingredients that can be utilized in any of the embodiments described herein include: hyaluronic acid, growth factors (e.g. VEGF, TGF family), therapeutic antibodies (e.g., Humira), substance P, glucosamine, chondroitin sulphate, glycosaminoglycans, pain control agents (e.g morphine), synovial fluid and/or its components, steroids and derivatives. It should further be understood that the combinations which are to be included within this invention are those combinations useful for their intended purpose. The agents set forth below are illustrative for purposes and not intended to be limited. The combinations which are part of this invention can be the compositions provided by the present invention and at least one additional agent selected from the lists below. The combination can also include more than one additional agent, e.g., two or three additional agents if the combination is such that the formed composition can perform its intended function.

Thus, in additional embodiments, the compositions provided by the invention can optionally further comprise an effective amount of at least one compound or protein selected from at least one of an anti-infective drug, a cardiovascular (CV) system drug, a central nervous system (CNS) drug, an autonomic nervous system (ANS) drug, a respiratory tract drug, a gastrointestinal (GI) tract drug, a hormonal drug, a drug for fluid or electrolyte balance, a hematologic drug, an antineoplastic, an immunomodulation drug, an ophthalmic, otic or nasal drug, a topical drug, a nutritional drug or the like. Such drugs are well known in the art, including formulations, indications, dosing and administration for each presented herein (see, e.g., Nursing 2001 Handbook of Drugs, 21.sup.st edition, Springhouse Corp., Springhouse, Pa., 2001; Health Professional's Drug Guide 2001, ed., Shannon, Wilson, Stang, Prentice-Hall, Inc, Upper Saddle River, N.J.; Pharmcotherapy Handbook, Wells et al., ed., Appleton & Lange, Stamford, Conn., each entirely incorporated herein by reference).

The anti-infective drug can be at least one selected from amebicides or at least one antiprotozoals, anthelmintics, antifungals, antimalarials, antituberculotics or at least one antileprotics, aminoglycosides, penicillins, cephalosporins, tetracyclines, sulfonamides, fluoroquinolones, antivirals, macrolide anti-infectives, and miscellaneous anti-infectives. The CV drug can be at least one selected from inotropics, antiarrhythmics, antianginals, antihypertensives, antilipemics, and miscellaneous cardiovascular drugs. The CNS drug can be at least one selected from normarcotic analgesics or at least one selected from antipyretics, nonsteroidal anti-inflammatory drugs, narcotic or at least one opioid analgesics, sedative-hypnotics, anticonvulsants, antidepressants, antianxiety drugs, antipsychotics, central nervous system stimulants, antiparkinsonians, and miscellaneous central nervous system drugs. The ANS drug can be at least one selected from cholinergics (parasympathomimetics), anticholinergics, adrenergics (sympathomimetics), adrenergic blockers (sympatholytics), skeletal muscle relaxants, and neuromuscular blockers. The respiratory tract drug can be at least one selected from antihistamines, bronchodilators, expectorants or at least one antitussive, and miscellaneous respiratory drugs. The GI tract drug can be at least one selected from antacids or at least one adsorbent or at least one antiflatulent, digestive enzyme or at least one gallstone solubilizer, antidiarrheals, laxatives, antiemetics, and antiulcer drugs. The hormonal drug can be at least one selected from corticosteroids, androgens or at least one anabolic steroid, estrogen or at least one progestin, gonadotropin, antidiabetic drug or at least one glucagon, thyroid hormone, thyroid hormone antagonist, pituitary hormone, and parathyroid-like drug. The drug for fluid and electrolyte balance can be at least one selected from diuretics, electrolytes or at least one replacement solution, acidifier or at least one alkalinizer. The hematologic drug can be at least one selected from hematinics, anticoagulants, blood derivatives, and thrombolytic enzymes. The antineoplastics can be at least one selected from alkylating drugs, antimetabolites, antibiotic antineoplastics, antineoplastics that alter hormone balance, and miscellaneous antineoplastics. The immunomodulation drug can be at least one selected from immunosuppressants, vaccines or at least one toxoid, antitoxin or at least one antivenin, immune serum, and biological response modifier. The ophthalmic, otic, and nasal drugs can be at least one selected from ophthalmic anti-infectives, ophthalmic anti-inflammatories, miotics, mydriatics, ophthalmic vasoconstrictors, miscellaneous ophthalmics, otics, and nasal drugs. The topical drug can be at least one selected from local anti-infectives, scabicides or at least one pediculicide or topical corticosteroid. The nutritional drug can be at least one selected from vitamins, minerals, or calorics. See, e.g., contents of Nursing 2001 Drug Handbook, supra.

The at least one amebicide or antiprotozoal can be at least one selected from atovaquone, chloroquine hydrochloride, chloroquine phosphate, metronidazole, metronidazole hydrochloride, and pentamidine isethionate. The at least one anthelmintic can be at least one selected from mebendazole, pyrantel pamoate, and thiabendazole. The at least one antifungal can be at least one selected from amphotericin B, amphotericin B cholesteryl sulfate complex, amphotericin B lipid complex, amphotericin B liposomal, fluconazole, flucytosine, griseofulvin microsize, griseofulvin ultramicrosize, itraconazole, ketoconazole, nystatin, and terbinafine hydrochloride. The at least one antimalarial can be at least one selected from chloroquine hydrochloride, chloroquine phosphate, doxycycline, hydroxychloroquine sulfate, mefloquine hydrochloride, primaquine phosphate, pyrimethamine, and pyrimethamine with sulfadoxine. The at least one antituberculotic or antileprotic can be at least one selected from clofazimine, cycloserine, dapsone, ethambutol hydrochloride, isoniazid, pyrazinamide, rifabutin, rifampin, rifapentine, and streptomycin sulfate. The at least one aminoglycoside can be at least one selected from amikacin sulfate, gentamicin sulfate, neomycin sulfate, streptomycin sulfate, and tobramycin sulfate. The at least one penicillin can be at least one selected from amoxcillin/clavulanate potassium, amoxicillin trihydrate, ampicillin, ampicillin sodium, ampicillin trihydrate, ampicillin sodium/sulbactam sodium, cloxacillin sodium, dicloxacillin sodium, mezlocillin sodium, nafcillin sodium, oxacillin sodium, penicillin G benzathine, penicillin G potassium, penicillin G procaine, penicillin G sodium, penicillin V potassium, piperacillin sodium, piperacillin sodium/tazobactam sodium, ticarcillin disodium, and ticarcillin disodium/clavulanate potassium.

The at least one cephalosporin can be at least one selected from cefaclor, cefadroxil, cefazolin sodium, cefdinir, cefepime hydrochloride, cefixime, cefinetazole sodium, cefonicid sodium, cefoperazone sodium, cefotaxime sodium, cefotetan disodium, cefoxitin sodium, cefpodoxime proxetil, cefprozil, ceftazidime, ceftibuten, ceftizoxime sodium, ceftriaxone sodium, cefuroxime axetil, cefuroxime sodium, cephalexin hydrochloride, cephalexin monohydrate, cephradine, and loracarbef. The at least one tetracycline can be at least one selected from demeclocycline hydrochloride, doxycycline calcium, doxycycline hyclate, doxycycline hydrochloride, doxycycline monohydrate, minocycline hydrochloride, and tetracycline hydrochloride. The at least one sulfonamide can be at least one selected from co-trimoxazole, sulfadiazine, sulfamethoxazole, sulfisoxazole, and sulfisoxazole acetyl. The at least one fluoroquinolone can be at least one selected from alatrofloxacin mesylate, ciprofloxacin, enoxacin, levofloxacin, lomefloxacin hydrochloride, nalidixic acid, norfloxacin, ofloxacin, sparfloxacin, and trovafloxacin mesylate. The at least one fluoroquinolone can be at least one selected from alatrofloxacin mesylate, ciprofloxacin, enoxacin, levofloxacin, lomefloxacin hydrochloride, nalidixic acid, norfloxacin, ofloxacin, sparfloxacin, and trovafloxacin mesylate. The at least one antiviral can be at least one selected from abacavir sulfate, acyclovir sodium, amantadine hydrochloride, amprenavir, cidofovir, delavirdine mesylate, didanosine, efavirenz, famciclovir, fomivirsen sodium, foscarnet sodium, ganciclovir, indinavir sulfate, lamivudine, lamivudine/zidovudine, nelfinavir mesylate, nevirapine, oseltamivir phosphate, ribavirin, rimantadine hydrochloride, ritonavir, saquinavir, saquinavir mesylate, stavudine, valacyclovir hydrochloride, zalcitabine, zanamivir, and zidovudine. The at least one macroline anti-infective can be at least one selected from azithromycin, clarithromycin, dirithromycin, erythromycin base, erythromycin estolate, erythromycin ethylsuccinate, erythromycin lactobionate, and erythromycin stearate. The at least one miscellaneous anti-infective can be at least one selected from aztreonam, bacitracin, chloramphenicol sodium sucinate, clindamycin hydrochloride, clindamycin palmitate hydrochloride, clindamycin phosphate, imipenem and cilastatin sodium, meropenem, nitrofurantoin macrocrystals, nitrofurantoin microcrystals, quinupristin/dalfopristin, spectinomycin hydrochloride, trimethoprim, and vancomycin hydrochloride. (See, e.g., pp. 24-214 of Nursing 2001 Drug Handbook.)

The at least one inotropic can be at least one selected from aminone lactate, digoxin, and milrinone lactate. The at least one antiarrhythmic can be at least one selected from adenosine, amiodarone hydrochloride, atropine sulfate, bretylium tosylate, diltiazem hydrochloride, disopyramide, disopyramide phosphate, esmolol hydrochloride, flecamide acetate, ibutilide fumarate, lidocaine hydrochloride, mexiletine hydrochloride, moricizine hydrochloride, phenyloin, phenyloin sodium, procainamide hydrochloride, propafenone hydrochloride, propranolol hydrochloride, quinidine bisulfate, quinidine gluconate, quinidine polygalacturonate, quinidine sulfate, sotalol, tocamide hydrochloride, and verapamil hydrochloride. The at least one antianginal can be at least one selected from amlodipidine besylate, amyl nitrite, bepridil hydrochloride, diltiazem hydrochloride, isosorbide dinitrate, isosorbide mononitrate, nadolol, nicardipine hydrochloride, nifedipine, nitroglycerin, propranolol hydrochloride, verapamil, and verapamil hydrochloride. The at least one antihypertensive can be at least one selected from acebutolol hydrochloride, amlodipine besylate, atenolol, benazepril hydrochloride, betaxolol hydrochloride, bisoprolol fumarate, candesartan cilexetil, captopril, carteolol hydrochloride, carvedilol, clonidine, clonidine hydrochloride, diazoxide, diltiazem hydrochloride, doxazosin mesylate, enalaprilat, enalapril maleate, eprosartan mesylate, felodipine, fenoldopam mesylate, fosinopril sodium, guanabenz acetate, guanadrel sulfate, guanfacine hydrochloride, hydralazine hydrochloride, irbesartan, isradipine, labetalol hydrochloride, lisinopril, losartan potassium, methyldopa, methyldopate hydrochloride, metoprolol succinate, metoprolol tartrate, minoxidil, moexipril hydrochloride, nadolol, nicardipine hydrochloride, nifedipine, nisoldipine, nitroprusside sodium, penbutolol sulfate, perindopril erbumine, phentolamine mesylate, pindolol, prazosin hydrochloride, propranolol hydrochloride, quinapril hydrochloride, ramipril, telmisartan, terazosin hydrochloride, timolol maleate, trandolapril, valsartan, and verapamil hydrochloride. The at least one antilipemic can be at least one selected from atorvastatin calcium, cerivastatin sodium, cholestyramine, colestipol hydrochloride, fenofibrate (micronized), fluvastatin sodium, gemfibrozil, lovastatin, niacin, pravastatin sodium, and simvastatin. The at least one miscellaneous CV drug can be at least one selected from abciximab, alprostadil, arbutamine hydrochloride, cilostazol, clopidogrel bisulfate, dipyridamole, eptifibatide, midodrine hydrochloride, pentoxifylline, ticlopidine hydrochloride, and tirofiban hydrochloride. (See, e.g., pp. 215-336 of Nursing 2001 Drug Handbook.)

The at least one normarcotic analgesic or antipyretic can be at least one selected from acetaminophen, aspirin, choline magnesium trisalicylate, diflunisal, and magnesium salicylate. The at least one nonsteroidal anti-inflammatory drug can be at least one selected from celecoxib, diclofenac potassium, diclofenac sodium, etodolac, fenoprofen calcium, flurbiprofen, ibuprofen, indomethacin, indomethacin sodium trihydrate, ketoprofen, ketorolac tromethamine, nabumetone, naproxen, naproxen sodium, oxaprozin, piroxicam, rofecoxib, and sulindac. The at least one narcotic or opioid analgesic can be at least one selected from alfentanil hydrochloride, buprenorphine hydrochloride, butorphanol tartrate, codeine phosphate, codeine sulfate, fentanyl citrate, fentanyl transdermal system, fentanyl transmucosal, hydromorphone hydrochloride, meperidine hydrochloride, methadone hydrochloride, morphine hydrochloride, morphine sulfate, morphine tartrate, nalbuphine hydrochloride, oxycodone hydrochloride, oxycodone pectinate, oxymorphone hydrochloride, pentazocine hydrochloride, pentazocine hydrochloride and naloxone hydrochloride, pentazocine lactate, propoxyphene hydrochloride, propoxyphene napsylate, remifentanil hydrochloride, sufentanil citrate, and tramadol hydrochloride. The at least one sedative-hypnotic can be at least one selected from chloral hydrate, estazolam, flurazepam hydrochloride, pentobarbital, pentobarbital sodium, phenobarbital sodium, secobarbital sodium, temazepam, triazolam, zaleplon, and zolpidem tartrate. The at least one anticonvulsant can be at least one selected from acetazolamide sodium, carbamazepine, clonazepam, clorazepate dipotassium, diazepam, divalproex sodium, ethosuximde, fosphenyloin sodium, gabapentin, lamotrigine, magnesium sulfate, phenobarbital, phenobarbital sodium, phenyloin, phenyloin sodium, phenyloin sodium (extended), primidone, tiagabine hydrochloride, topiramate, valproate sodium, and valproic acid. The at least one antidepressant can be at least one selected from amitriptyline hydrochloride, amitriptyline pamoate, amoxapine, bupropion hydrochloride, citalopram hydrobromide, clomipramine hydrochloride, desipramine hydrochloride, doxepin hydrochloride, fluoxetine hydrochloride, imipramine hydrochloride, imipramine pamoate, mirtazapine, nefazodone hydrochloride, nortriptyline hydrochloride, paroxetine hydrochloride, phenelzine sulfate, sertraline hydrochloride, tranylcypromine sulfate, trimipramine maleate, and venlafaxine hydrochloride. The at least one antianxiety drug can be at least one selected from alprazolam, buspirone hydrochloride, chlordiazepoxide, chlordiazepoxide hydrochloride, clorazepate dipotassium, diazepam, doxepin hydrochloride, hydroxyzine embonate, hydroxyzine hydrochloride, hydroxyzine pamoate, lorazepam, mephrobamate, midazolam hydrochloride, and oxazepam. The at least one antipsychotic drug can be at least one selected from chlorpromazine hydrochloride, clozapine, fluphenazine decanoate, fluephenazine enanthate, fluphenazine hydrochloride, haloperidol, haloperidol decanoate, haloperidol lactate, loxapine hydrochloride, loxapine succinate, mesoridazine besylate, molindone hydrochloride, olanzapine, perphenazine, pimozide, prochlorperazine, quetiapine fumarate, risperidone, thioridazine hydrochloride, thiothixene, thiothixene hydrochloride, and trifluoperazine hydrochloride. The at least one central nervous system stimulant can be at least one selected from amphetamine sulfate, caffeine, dextroamphetamine sulfate, doxapram hydrochloride, methamphetamine hydrochloride, methylphenidate hydrochloride, modafinil, pemoline, and phentermine hydrochloride. The at least one antiparkinsonian can be at least one selected from amantadine hydrochloride, benztropine mesylate, biperiden hydrochloride, biperiden lactate, bromocriptine mesylate, carbidopa-levodopa, entacapone, levodopa, pergolide mesylate, pramipexole dihydrochloride, ropinirole hydrochloride, selegiline hydrochloride, tolcapone, and trihexyphenidyl hydrochloride. The at least one miscellaneous central nervous system drug can be at least one selected from bupropion hydrochloride, donepezil hydrochloride, droperidol, fluvoxamine maleate, lithium carbonate, lithium citrate, naratriptan hydrochloride, nicotine polacrilex, nicotine transdermal system, propofol, rizatriptan benzoate, sibutramine hydrochloride monohydrate, sumatriptan succinate, tacrine hydrochloride, and zolmitriptan. (See, e.g., pp. 337-530 of Nursing 2001 Drug Handbook.)

The at least one cholinergic (e.g., parasympathomimetic) can be at least one selected from bethanechol chloride, edrophonium chloride, neostigmine bromide, neostigmine methylsulfate, physostigmine salicylate, and pyridostigmine bromide. The at least one anticholinergic can be at least one selected from atropine sulfate, dicyclomine hydrochloride, glycopyrrolate, hyoscyamine, hyoscyamine sulfate, propantheline bromide, scopolamine, scopolamine butylbromide, and scopolamine hydrobromide. The at least one adrenergic (sympathomimetics) can be at least one selected from dobutamine hydrochloride, dopamine hydrochloride, metaraminol bitartrate, norepinephrine bitartrate, phenylephrine hydrochloride, pseudoephedrine hydrochloride, and pseudoephedrine sulfate. The at least one adrenergic blocker (sympatholytic) can be at least one selected from dihydroergotamine mesylate, ergotamine tartrate, methysergide maleate, and propranolol hydrochloride. The at least one skeletal muscle relaxant can be at least one selected from baclofen, carisoprodol, chlorzoxazone, cyclobenzaprine hydrochloride, dantrolene sodium, methocarbamol, and tizanidine hydrochloride. The at least one neuromuscular blocker can be at least one selected from atracurium besylate, cisatracurium besylate, doxacurium chloride, mivacurium chloride, pancuronium bromide, pipecuronium bromide, rapacuronium bromide, rocuronium bromide, succinylcholine chloride, tubocurarine chloride, and vecuronium bromide. (See, e.g., pp. 531-84 of Nursing 2001 Drug Handbook.)

The at least one antihistamine can be at least one selected from brompheniramine maleate, cetirizine hydrochloride, chlorpheniramine maleate, clemastine fumarate, cyproheptadine hydrochloride, diphenhydramine hydrochloride, fexofenadine hydrochloride, loratadine, promethazine hydrochloride, promethazine theoclate, and triprolidine hydrochloride. The at least one bronchodilator can be at least one selected from albuterol, albuterol sulfate, aminophylline, atropine sulfate, ephedrine sulfate, epinephrine, epinephrine bitartrate, epinephrine hydrochloride, ipratropium bromide, isoproterenol, isoproterenol hydrochloride, isoproterenol sulfate, levalbuterol hydrochloride, metaproterenol sulfate, oxtriphylline, pirbuterol acetate, salmeterol xinafoate, terbutaline sulfate, and theophylline. The at least one expectorant or antitussive can be at least one selected from benzonatate, codeine phosphate, codeine sulfate, dextramethorphan hydrobromide, diphenhydramine hydrochloride, guaifenesin, and hydromorphone hydrochloride. The at least one miscellaneous respiratory drug can be at least one selected from acetylcysteine, beclomethasone dipropionate, beractant, budesonide, calfactant, cromolyn sodium, domase alfa, epoprostenol sodium, flunisolide, fluticasone propionate, montelukast sodium, nedocromil sodium, palivizumab, triamcinolone acetonide, zafirlukast, and zileuton. (See, e.g., pp. 585-642 of Nursing 2001 Drug Handbook.)

The at least one antacid, adsorbent, or antiflatulent can be at least one selected from aluminum carbonate, aluminum hydroxide, calcium carbonate, magaldrate, magnesium hydroxide, magnesium oxide, simethicone, and sodium bicarbonate. The at least one digestive enzyme or gallstone solubilizer can be at least one selected from pancreatin, pancrelipase, and ursodiol. The at least one antidiarrheal can be at least one selected from attapulgite, bismuth subsalicylate, calcium polycarbophil, diphenoxylate hydrochloride and atropine sulfate, loperamide, octreotide acetate, opium tincture, and opium tincure (camphorated). The at least one laxative can be at least one selected from bisocodyl, calcium polycarbophil, cascara sagrada, cascara sagrada aromatic fluidextract, cascara sagrada fluidextract, castor oil, docusate calcium, docusate sodium, glycerin, lactulose, magnesium citrate, magnesium hydroxide, magnesium sulfate, methylcellulose, mineral oil, polyethylene glycol or electrolyte solution, psyllium, senna, and sodium phosphates. The at least one antiemetic can be at least one selected from chlorpromazine hydrochloride, dimenhydrinate, dolasetron mesylate, dronabinol, granisetron hydrochloride, meclizine hydrochloride, metocloproamide hydrochloride, ondansetron hydrochloride, perphenazine, prochlorperazine, prochlorperazine edisylate, prochlorperazine maleate, promethazine hydrochloride, scopolamine, thiethylperazine maleate, and trimethobenzamide hydrochloride. The at least one antiulcer drug can be at least one selected from cimetidine, cimetidine hydrochloride, famotidine, lansoprazole, misoprostol, nizatidine, omeprazole, rabeprozole sodium, rantidine bismuth citrate, ranitidine hydrochloride, and sucralfate. (See, e.g., pp. 643-95 of Nursing 2001 Drug Handbook.)

The at least one coricosteroid can be at least one selected from betamethasone, betamethasone acetate or betamethasone sodium phosphate, betamethasone sodium phosphate, cortisone acetate, dexamethasone, dexamethasone acetate, dexamethasone sodium phosphate, fludrocortisone acetate, hydrocortisone, hydrocortisone acetate, hydrocortisone cypionate, hydrocortisone sodium phosphate, hydrocortisone sodium succinate, methylprednisolone, methylprednisolone acetate, methylprednisolone sodium succinate, prednisolone, prednisolone acetate, prednisolone sodium phosphate, prednisolone tebutate, prednisone, triamcinolone, triamcinolone acetonide, and triamcinolone diacetate. The at least one androgen or anabolic steroid can be at least one selected from danazol, fluoxymesterone, methyltestosterone, nandrolone decanoate, nandrolone phenpropionate, testosterone, testosterone cypionate, testosterone enanthate, testosterone propionate, and testosterone transdermal system. The at least one estrogen or progestin can be at least one selected from esterified estrogens, estradiol, estradiol cypionate, estradiol/norethindrone acetate transdermal system, estradiol valerate, estrogens (conjugated), estropipate, ethinyl estradiol, ethinyl estradiol and desogestrel, ethinyl estradiol and ethynodiol diacetate, ethinyl estradiol and desogestrel, ethinyl estradiol and ethynodiol diacetate, ethinyl estradiol and levonorgestrel, ethinyl estradiol and norethindrone, ethinyl estradiol and norethindrone acetate, ethinyl estradiol and norgestimate, ethinyl estradiol and norgestrel, ethinyl estradiol and norethindrone and acetate and ferrous fumarate, levonorgestrel, medroxyprogesterone acetate, mestranol and norethindron, norethindrone, norethindrone acetate, norgestrel, and progesterone. The at least one gonadroptropin can be at least one selected from ganirelix acetate, gonadoreline acetate, histrelin acetate, and menotropins. The at least one antidiabetic or glucaon can be at least one selected from acarbose, chlorpropamide, glimepiride, glipizide, glucagon, glyburide, insulins, metformin hydrochloride, miglitol, pioglitazone hydrochloride, repaglinide, rosiglitazone maleate, and troglitazone. The at least one thyroid hormone can be at least one selected from levothyroxine sodium, liothyronine sodium, liotrix, and thyroid. The at least one thyroid hormone antagonist can be at least one selected from methimazole, potassium iodide, potassium iodide (saturated solution), propylthiouracil, radioactive iodine (sodium iodide. sup.131I), and strong iodine solution. The at least one pituitary hormone can be at least one selected from corticotropin, cosyntropin, desmophressin acetate, leuprolide acetate, repository corticotropin, somatrem, somatropin, and vasopressin. The at least one parathyroid-like drug can be at least one selected from calcifediol, calcitonin (human), calcitonin (salmon), calcitriol, dihydrotachysterol, and etidronate disodium. (See, e.g., pp. 696-796 of Nursing 2001 Drug Handbook.)

The at least one diuretic can be at least one selected from acetazolamide, acetazolamide sodium, amiloride hydrochloride, bumetanide, chlorthalidone, ethacrynate sodium, ethacrynic acid, furosemide, hydrochlorothiazide, indapamide, mannitol, metolazone, spironolactone, torsemide, triamterene, and urea. The at least one electrolyte or replacement solution can be at least one selected from calcium acetate, calcium carbonate, calcium chloride, calcium citrate, calcium glubionate, calcium gluceptate, calcium gluconate, calcium lactate, calcium phosphate (dibasic), calcium phosphate (tribasic), dextran (high-molecular-weight), dextran (low-molecular-weight), hetastarch, magnesium chloride, magnesium sulfate, potassium acetate, potassium bicarbonate, potassium chloride, potassium gluconate, Ringer's injection, Ringer's injection (lactated), and sodium chloride. The at least one acidifier or alkalinizer can be at least one selected from sodium bicarbonate, sodium lactate, and tromethamine. (See, e.g., pp. 797-833 of Nursing 2001 Drug Handbook.)

The at least one hematinic can be at least one selected from ferrous fumarate, ferrous gluconate, ferrous sulfate, ferrous sulfate (dried), iron dextran, iron sorbitol, polysaccharide-iron complex, and sodium ferric gluconate complex. The at least one anticoagulant can be at least one selected from ardeparin sodium, dalteparin sodium, danaparoid sodium, enoxaparin sodium, heparin calcium, heparin sodium, and warfarin sodium. The at least one blood derivative can be at least one selected from albumin 5%, albumin 25%, antihemophilic factor, anti-inhibitor coagulant complex, antithrombin III (human), factor IX (human), factor IX complex, and plasma protein fractions. The at least one thrombolytic enzyme can be at least one selected from alteplase, anistreplase, reteplase (recombinant), streptokinase, and urokinase. (See, e.g., pp. 834-66 of Nursing 2001 Drug Handbook.)

The at least one alkylating drug can be at least one selected from busulfan, carboplatin, carmustine, chlorambucil, cisplatin, cyclophosphamide, ifosfamide, lomustine, mechlorethamine hydrochloride, melphalan, melphalan hydrochloride, streptozocin, temozolomide, and thiotepa. The at least one antimetabolite can be at least one selected from capecitabine, cladribine, cytarabine, floxuridine, fludarabine phosphate, fluorouracil, hydroxyurea, mercaptopurine, methotrexate, methotrexate sodium, and thioguanine. The at least one antibiotic antineoplastic can be at least one selected from bleomycin sulfate, dactinomycin, daunorubicin citrate liposomal, daunorubicin hydrochloride, doxorubicin hydrochloride, doxorubicin hydrochloride liposomal, epirubicin hydrochloride, idarubicin hydrochloride, mitomycin, pentostatin, plicamycin, and valrubicin. The at least one antineoplastic that alters hormone balance can be at least one selected from anastrozole, bicalutamide, estramustine phosphate sodium, exemestane, flutamide, goserelin acetate, letrozole, leuprolide acetate, megestrol acetate, nilutamide, tamoxifen citrate, testolactone, and toremifene citrate. The at least one miscellaneous antineoplastic can be at least one selected from asparaginase, bacillus Calmette-Guerin (BCG) (live intravesical), dacarbazine, docetaxel, etoposide, etoposide phosphate, gemcitabine hydrochloride, irinotecan hydrochloride, mitotane, mitoxantrone hydrochloride, paclitaxel, pegaspargase, porfimer sodium, procarbazine hydrochloride, rituximab, teniposide, topotecan hydrochloride, trastuzumab, tretinoin, vinblastine sulfate, vincristine sulfate, and vinorelbine tartrate. (See, e.g., pp. 867-963 of Nursing 2001 Drug Handbook.)

The at least one immunosuppressant can be at least one selected from azathioprine, basiliximab, cyclosporine, daclizumab, lymphocyte immune globulin, muromonab-CD3, mycophenolate mofetil, mycophenolate mofetil hydrochloride, sirolimus, and tacrolimus. The at least one vaccine or toxoid can be at least one selected from BCG vaccine, cholera vaccine, diphtheria and tetanus toxoids (adsorbed), diphtheria and tetanus toxoids and acellular pertussis vaccine adsorbed, diphtheria and tetanus toxoids and whole-cell pertussis vaccine, Haemophilus b conjugate vaccines, hepatitis A vaccine (inactivated), hepatitis B vaccine (recombinant), influenza virus vaccine 1999-2000 trivalent types A & B (purified surface antigen), influenza virus vaccine 1999-2000 trivalent types A & B (subvirion or purified subvirion), influenza virus vaccine 1999-2000 trivalent types A & B (whole virion), Japanese encephalitis virus vaccine (inactivated), Lyme disease vaccine (recombinant OspA), measles and mumps and rubella virus vaccine (live), measles and mumps and rubella virus vaccine (live attenuated), measles virus vaccine (live attenuated), meningococcal polysaccharide vaccine, mumps virus vaccine (live), plague vaccine, pneumococcal vaccine (polyvalent), poliovirus vaccine (inactivated), poliovirus vaccine (live, oral, trivalent), rabies vaccine (adsorbed), rabies vaccine (human diploid cell), rubella and mumps virus vaccine (live), rubella virus vaccine (live, attenuated), tetanus toxoid (adsorbed), tetanus toxoid (fluid), typhoid vaccine (oral), typhoid vaccine (parenteral), typhoid Vi polysaccharide vaccine, varicella virus vaccine, and yellow fever vaccine. The at least one antitoxin or antivenin can be at least one selected from black widow spider antivenin, Crotalidae antivenom (polyvalent), diphtheria antitoxin (equine), and Micrurus fulvius antivenin. The at least one immune serum can be at least one selected from cytomegalovirus immune globulin (intravenous), hepatitis B immune globulin (human), immune globulin intramuscular, immune globulin intravenous, rabies immune globulin (human), respiratory syncytial virus immune globulin intravenous (human), Rh.sub.0(D) immune globulin (human), Rh.sub.0(D) immune globulin intravenous (human), tetanus immune globulin (human), and varicella-zoster immune globulin. The at least one biological response modifier can be at least one selected from aldesleukin, epoetin alfa, filgrastim, glatiramer acetate for injection, interferon alfacon-1, interferon alfa-2a (recombinant), interferon alfa-2b (recombinant), interferon beta-1a, interferon beta-1b (recombinant), interferon gamma-1b, levamisole hydrochloride, oprelvekin, and sargramostim. (See, e.g., pp. 964-1040 of Nursing 2001 Drug Handbook.)

The at least one ophthalmic anti-infective can be selected form bacitracin, chloramphenicol, ciprofloxacin hydrochloride, erythromycin, gentamicin sulfate, ofloxacin 0.3%, polymyxin B sulfate, sulfacetamide sodium 10%, sulfacetamide sodium 15%, sulfacetamide sodium 30%, tobramycin, and vidarabine. The at least one ophthalmic anti-inflammatory can be at least one selected from dexamethasone, dexamethasone sodium phosphate, diclofenac sodium 0.1%, fluorometholone, flurbiprofen sodium, ketorolac tromethamine, prednisolone acetate (suspension) and prednisolone sodium phosphate (solution). The at least one miotic can be at least one selected from acetylocholine chloride, carbachol (intraocular), carbachol (topical), echothiophate iodide, pilocarpine, pilocarpine hydrochloride, and pilocarpine nitrate. The at least one mydriatic can be at least one selected from atropine sulfate, cyclopentolate hydrochloride, epinephrine hydrochloride, epinephryl borate, homatropine hydrobromide, phenylephrine hydrochloride, scopolamine hydrobromide, and tropicamide. The at least one ophthalmic vasoconstrictor can be at least one selected from naphazoline hydrochloride, oxymetazoline hydrochloride, and tetrahydrozoline hydrochloride. The at least one miscellaneous ophthalmic can be at least one selected from apraclonidine hydrochloride, betaxolol hydrochloride, brimonidine tartrate, carteolol hydrochloride, dipivefrin hydrochloride, dorzolamide hydrochloride, emedastine difumarate, fluorescein sodium, ketotifen fumarate, latanoprost, levobunolol hydrochloride, metipranolol hydrochloride, sodium chloride (hypertonic), and timolol maleate. The at least one otic can be at least one selected from boric acid, carbamide peroxide, chloramphenicol, and triethanolamine polypeptide oleate-condensate. The at least one nasal drug can be at least one selected from beclomethasone dipropionate, budesonide, ephedrine sulfate, epinephrine hydrochloride, flunisolide, fluticasone propionate, naphazoline hydrochloride, oxymetazoline hydrochloride, phenylephrine hydrochloride, tetrahydrozoline hydrochloride, triamcinolone acetonide, and xylometazoline hydrochloride. (See, e.g., pp. 1041-97 of Nursing 2001 Drug Handbook.)

The at least one local anti-infective can be at least one selected from acyclovir, amphotericin B, azelaic acid cream, bacitracin, butoconazole nitrate, clindamycin phosphate, clotrimazole, econazole nitrate, erythromycin, gentamicin sulfate, ketoconazole, mafenide acetate, metronidazole (topical), miconazole nitrate, mupirocin, naftifine hydrochloride, neomycin sulfate, nitrofurazone, nystatin, silver sulfadiazine, terbinafine hydrochloride, terconazole, tetracycline hydrochloride, tioconazole, and tolnaftate. The at least one scabicide or pediculicide can be at least one selected from crotamiton, lindane, permethrin, and pyrethrins. The at least one topical corticosteroid can be at least one selected from betamethasone dipropionate, betamethasone valerate, clobetasol propionate, desonide, desoximetasone, dexamethasone, dexamethasone sodium phosphate, diflorasone diacetate, fluocinolone acetonide, fluocinonide, flurandrenolide, fluticasone propionate, halcionide, hydrocortisone, hydrocortisone acetate, hydrocortisone butyrate, hydrocorisone valerate, mometasone furoate, and triamcinolone acetonide. (See, e.g., pp. 1098-1136 of Nursing 2001 Drug Handbook.)

The at least one vitamin or mineral can be at least one selected from vitamin A, vitamin B complex, cyanocobalamin, folic acid, hydroxocobalamin, leucovorin calcium, niacin, niacinamide, pyridoxine hydrochloride, riboflavin, thiamine hydrochloride, vitamin C, vitamin D, cholecalciferol, ergocalciferol, vitamin D analogue, doxercalciferol, paricalcitol, vitamin E, vitamin K analogue, phytonadione, sodium fluoride, sodium fluoride (topical), trace elements, chromium, copper, iodine, manganese, selenium, and zinc. The at least one caloric can be at least one selected from amino acid infusions (crystalline), amino acid infusions in dextrose, amino acid infusions with electrolytes, amino acid infusions with electrolytes in dextrose, amino acid infusions for hepatic failure, amino acid infusions for high metabolic stress, amino acid infusions for renal failure, dextrose, fat emulsions, and medium-chain triglycerides. (See, e.g., pp. 1137-63 of Nursing 2001 Drug Handbook.)

The compositions provided by the present invention can further comprise at least one of any suitable and effective amount of a composition or pharmaceutical composition comprising at least one of an anti-IL-12 antibody contacted or administered to a cell, tissue, organ, animal or patient in need of such modulation, treatment or therapy, a TNF antagonist (e.g., but not limited to a TNF chemical or protein antagonist, TNF monoclonal or polyclonal antibody or fragment, a soluble TNF receptor (e.g., p55, p70 or p85) or fragment, fusion polypeptides thereof, or a small molecule TNF antagonist, e.g., TNF binding protein I or II (TBP-1 or TBP-II), nerelimonmab, infliximab, etemacept, CDP-571, CDP-870, afelimomab, lenercept, and the like), an antirheumatic (e.g., methotrexate, auranofin, aurothioglucose, azathioprine, etanercept, gold sodium thiomalate, hydroxychloroquine sulfate, leflunomide, sulfasalzine), a muscle relaxant, a narcotic, a non-steroid anti-inflammatory drug (NSAID), an analgesic, an anesthetic, a sedative, a local anesthetic, a neuromuscular blocker, an antimicrobial (e.g., aminoglycoside, an antifungal, an antiparasitic, an antiviral, a carbapenem, cephalosporin, a fluororquinolone, a macrolide, a penicillin, a sulfonamide, a tetracycline, another antimicrobial), an antipsoriatic, a corticosteriod, an anabolic steroid, a diabetes related agent, a mineral, a nutritional, a thyroid agent, a vitamin, a calcium related hormone, an antidiarrheal, an antitussive, an antiemetic, an antiulcer, a laxative, an anticoagulant, an erythropoietin (e.g., epoetin alpha), a filgrastim (e.g., G-CSF, Neupogen), a sargramostim (GM-CSF, Leukine), an immunization, an immunoglobulin, an immunosuppressive (e.g., basiliximab, cyclosporine, daclizumab), a growth hormone, a hormone replacement drug, an estrogen receptor modulator, a mydriatic, a cycloplegic, an alkylating agent, an antimetabolite, a mitotic inhibitor, a radiopharmaceutical, an antidepressant, antimanic agent, an antipsychotic, an anxiolytic, a hypnotic, a sympathomimetic, a stimulant, donepezil, tacrine, an asthma medication, a beta agonist, an inhaled steroid, a leukotriene inhibitor, a methylxanthine, a cromolyn, an epinephrine or analog, dornase alpha (Pulmozyme), a cytokine or a cytokine antagonist. Non-limiting examples of such cytokines include, but are not limited to, any of IL-1 to IL-23 (e.g., IL-1, IL-2, etc.). Suitable dosages are well known in the art. See, e.g., Wells et al., eds., Pharmacotherapy Handbook, 2.sup.nd Edition, Appleton and Lange, Stamford, Conn. (2000); PDR Pharmacopoeia, Tarascon Pocket Pharmacopoeia 2000, Deluxe Edition, Tarascon Publishing, Loma Linda, Calif. (2000), each of which references are entirely incorporated herein by reference.

Such anti-cancer or anti-infectives can also include toxin molecules that are associated, bound, co-formulated or co-administered with at least one antibody of the present invention. The toxin can optionally act to selectively kill the pathologic cell or tissue. The pathologic cell can be a cancer or other cell. Such toxins can be, but are not limited to, purified or recombinant toxin or toxin fragment comprising at least one functional cytotoxic domain of toxin, e.g., selected from at least one of ricin, diphtheria toxin, a venom toxin, or a bacterial toxin. The term toxin also includes both endotoxins and exotoxins produced by any naturally occurring, mutant or recombinant bacteria or viruses which may cause any pathological condition in humans and other mammals, including toxin shock, which can result in death. Such toxins may include, but are not limited to, enterotoxigenic *E. coli* heat-labile enterotoxin (LT), heat-stable enterotoxin (ST), *Shigella cytotoxin, Aeromonas enterotoxins*, toxic shock syndrome toxin-1 (TSST-1), Staphylococcal enterotoxin A (SEA), B (SEB), or C (SEC), Streptococcal enterotoxins and the like. Such bacteria include, but are not limited to, strains of a species of enterotoxigenic *E. coli* (ETEC), enterohemorrhagic *E. coli* (e.g., strains of serotype 0157:H7), *Staphylococcus* species (e.g., *Staphylococcus aureus, Staphylococcus pyogenes*), *Shigella* species (e.g., *Shigella dysenteriae, Shigella flexneri, Shigella boydii*, and *Shigella sonnei*), *Salmonella* species (e.g., *Salmonella typhi, Salmonella cholerasuis, Salmonella enteritidis*), *Clostridium* species (e.g., *Clostridium perfringens, Clostridium dificile, Clostridium botulinum*), *Camphlobacter* species (e.g., *Camphlobacter jejuni, Camphlobacter fetus*), *Heliobacter* species, (e.g., *Heliobacter pylori*), *Aeromonas* species (e.g., *Aeromonas sobria, Aeromonas hydrophila, Aeromonas caviae*), *Pleisomonas shigelloides, Yersina enterocolitica, Vibrios* species (e.g., *Vibrios cholerae, Vibrios parahemolyticus*), *Klebsiella* species, *Pseudomonas aeruginosa*, and *Streptococci*. See, e.g., Stein, ed., INTERNAL MEDICINE, 3rd ed., pp 1-13, Little, Brown and Co., Boston, (1990); Evans et al., eds., Bacterial Infections of Humans: Epidemiology and Control, 2d. Ed., pp 239-254, Plenum Medical Book Co., New York (1991); Mandell et al, Principles and Practice of Infectious Diseases, 3d. Ed., Churchill Livingstone, New York (1990); Berkow et al, eds., The Merck Manual, 16th edition, Merck and Co., Rahway, N.J., 1992; Wood et al, FEMS Microbiology Immunology, 76:121-134 (1991); Marrack et al, Science, 248:705-711 (1990), the contents of which references are incorporated entirely herein by reference.

In any embodiment described herein, the compositions provided by the invention can be administered by any pharmaceutically acceptable route, for example, oral, anal, vaginal, nasal, enteral, parenteral, intravenous, intraperitoneal, sublingual, percutaneous, topical, via inhalation, and the like. Systemic formulations include those designed for administration by injection, e.g. subcutaneous, intravenous, intramuscular, intrathecal or intraperitoneal injection, as well as those designed for transdermal, transmucosal, oral or pulmonary administration. Similarly, the composition of the invention can be in any suitable form, for example, liquid, gel, cream, aerosol, lotion, and the like.

For injection, the solution may contain additional formulatory agents such as suspending, stabilizing and/or dispersing agents. Alternatively, the proteins may be in powder form for constitution with a suitable vehicle, e.g., sterile pyrogen-free water, before use.

For administration by inhalation, the composition for use according to the present invention are conveniently delivered in the form of an aerosol spray from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. For example, liposomes and emulsions are well known examples of delivery vehicles that may be used in conjunction with the composition of the invention to deliver a biologically active agent.

As used herein, an "effective amount" or "therapeutically effective dose" refers to that amount of the therapeutic sufficient to prevent, delay, inhibit the occurrence, or treat (alleviate a symptom to some extent, preferably all of the symptoms) of a disease state. The effective amount or dose depends on the type of disease, the composition used, the route of administration, the type of mammal being treated, the physical characteristics of the specific mammal under consideration, concurrent medication, and other factors which those skilled in the medical arts will recognize.

A suitable dose is an amount/rate/volume of the composition that, when administered as described above, is capable of ameliorating or reducing tissue and/or cellular damage observed with saline or Ringer's solution. Suitable dose rates of administration will also vary with a number of factors, for example, patient size, procedure type, duration, and the like. Dose rates will typically range from about 1 mL/min to about 500 mL/min. In general, the amount of composition administered in a dose will range from about 0.1 mL to about 500 mL per kg of host, typically from 1 mL to about 50 liters.

Determination of an effective amount of the composition of the invention for use in, for example, in vitro culture of cells or tissues, veterinary surgical procedures or human surgical procedures is well within the capabilities of those skilled in the art, especially in light of the detailed disclosure provided herein. An effective dose can be estimated initially from in vitro assays. For example, a dose and/or perfusion rate and volume can be formulated in animal models to achieve the desired amelioration of tissue and cellular damage using techniques that are well known in the art. One having ordinary skill in the art could readily optimize administration to humans based on animal data. Dosage amount and interval may be adjusted individually. For example, the invention may be administered in a single dose, multiple dosage administered at discrete time points, or administered continuously during a portion of or throughout the entire procedure. Alternate protocols may be appropriate for individual patients. A suitable dose is an amount/rate/volume of the composition that, when administered as described above, is capable of ameliorating or reducing tissue and/or cellular damage observed with saline or Ringer's solution.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds that exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects. The data obtained from the cell culture assays and animal studies can be used in formulating a range of dosage for use in humans. The dosage of such compounds lies preferably within a range of circulating concentrations that include the ED50 with little or no toxicity.

Generally, for an active ingredient an amount between 0.1 mg/kg and 1000 mg/kg body weight/day of active ingredients is administered dependent upon potency of the active ingredient(s). The dosage may vary within this range depending upon the particular API, dosage form employed, and the route of administration utilized. For any compound used in the method of the invention, the therapeutically effective dose can be estimated initially from cell culture, and/or animal assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

Determination of an effective amount of the composition of the invention for use in, for example, in vitro culture of cells or tissues, veterinary surgical procedures or human surgical procedures is well within the capabilities of those skilled in the art, especially in light of the detailed disclosure provided herein. An effective dose can be estimated initially from in vitro assays. For example, a dose and/or perfusion rate and volume can be formulated in animal models to achieve the desired amelioration of tissue and cellular damage using techniques that are well known in the art. One having ordinary skill in the art could readily optimize administration to humans based on animal data. Dosage amount and interval may be adjusted individually. For example, the invention may be administered in a single dose, multiple dosage administered at discrete time points, or administered continuously during a portion of or throughout the entire procedure. Alternate protocols may be appropriate for individual patients.

The contents of all references, patents, pending patent applications and published patents, cited throughout this application are hereby expressly incorporated by reference. Those skilled in the art will recognize, or be able to ascertain using no more than routine experimentation, many equivalents to the specific embodiments of the invention described herein. Such equivalents are intended to be encompassed by the following claims.

It is understood that the detailed examples and embodiments described herein are given by way of example for illustrative purposes only, and are in no way considered to be limiting to the invention. Various modifications or changes in light thereof will be suggested to persons skilled in the art and are included within the spirit and purview of this application and are considered within the scope of the appended claims. For example, the relative quantities of the ingredients may be varied to optimize the desired effects, additional ingredients may be added, and/or similar ingredients may be substituted for one or more of the ingredients described. Additional advantageous features and functionalities associated with the systems, methods, and processes of the present invention will be apparent from the appended claims. Moreover, those skilled in the art will recognize, or be able to ascertain using no more than routine experimentation, many equivalents to the specific embodiments of the invention described herein. Such equivalents are intended to be encompassed by the following claims.

EXAMPLES

The following non-limiting examples are described further, below, with reference to FIGS. 1-7. In particular, although the examples were performed using articular cartilage chondrocytes, the invention is not limited thereto. For example, as would be appreciated by the skilled artisan, the compositions provided by the invention would be suitable for use in procedures involving any cell or tissue type.

Example 1

FIG. 1 demonstrates the results obtained in assays using one embodiment of the present invention. In this exemplary embodiment, the composition comprises isotonic phosphate buffered saline, high molecular weight dextran, ascorbate, transferrin, and the poloxamer surfactant P188. In this experiment, full thickness discs (about 6 mm diameter) of articular cartilage from the bovine radial-carpal joint are immersed in various solutions for about 24 hours or about 48 hours, respectively. After the immersion step, the cartilage is cut into 70 μm sections on a vibratome and stained with Syto 13 (Molecular Probes) and ethidium bromide to assess chondrocyte viability.

FIG. 1 demonstrates the local anesthetic bupivacaine ((bup+PBS, 1.25 mg/mL [0.125%]) causes chondrocyte death at about 24 hours (approximately 35% chondrocytes death) and at about 48 hours (approximately 68.5% chondrocyte death) when articular cartilage is bathed in a solution of 1.25 mg/mL bupivacaine ([0.125%] phosphate buffered saline with bupivicaine). When the solution as provided by the invention is used with the same concentration of bupivacaine (bup+arthroguard), chondrocyte death is reduced to approximately 17% at about 24 hours and approximately 20% at about 48 hours.

The results indicate that the exemplary embodiment of the composition of the invention was surprisingly and unexpectedly successful at reducing or ameliorating cell death (necrosis and/or apoptosis) that occurs in the presence of anesthetic.

Example 2

FIG. 1 also demonstrates the observed results attained using another exemplary embodiment of the present invention. In particular, the adjuvant composition additionally comprises epinephrine, and bupivacaine. When epinephrine (5 ug/mL) is added to the solution of phosphate buffered saline with bupivacaine (1.25 mg/mL [0.125%]), chondrocyte death is approximately 53.5% at about 24 hours and approximately 97.5% at about 48 hours (bup/epi/PBS). On the other hand, when the cells are exposed to the arthroguard solution containing the same concentrations of epinephrine and bupivacaine (bup/epi/AG), chondrocyte death is reduced to approximately 29% at about 24 hours and approximately 48% at about 48 hours.

Example 3

Figure 2:
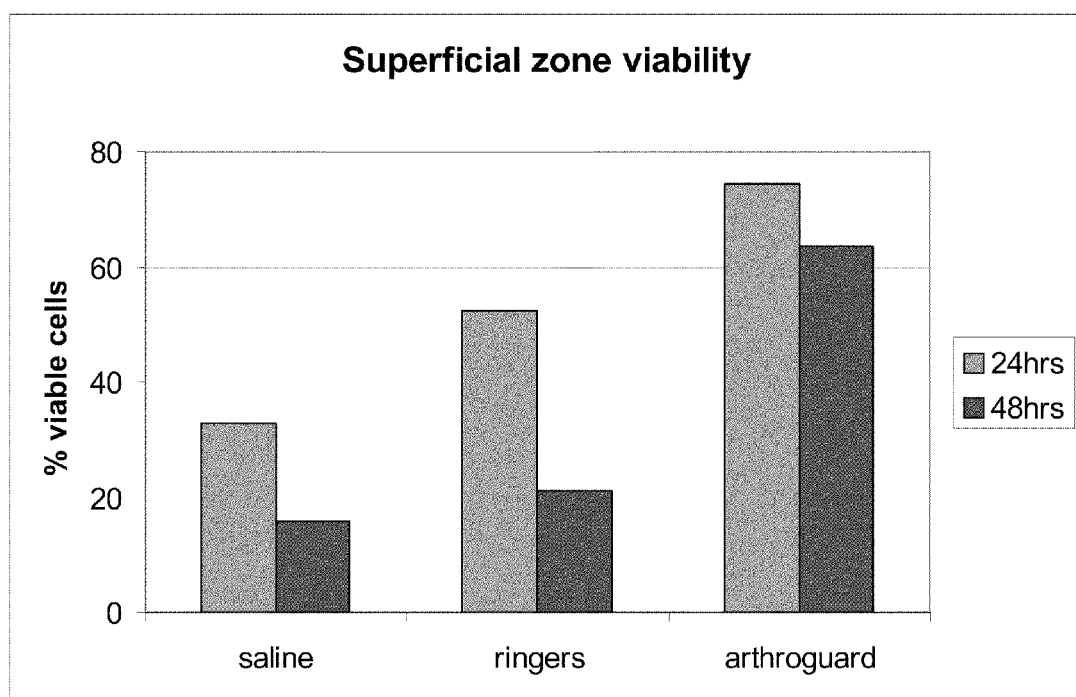
FIG. 2 demonstrates the effects of an exemplary composition provided by the invention (i.e., arthroguard) on chondrocyte death in the superficial zone after exposure to saline, and ringers. Full thickness discs (6 mm diameter) of articular cartilage from the bovine radial-carpal joint are immersed in various solutions for 24 and 48 hours, after which the cartilage is cut into 70 μm sections (sections cut perpendicular to the articular surface) on a vibratome and stained with Syto 13 (Molecular Probes) and ethidium bromide to assess chondrocyte viability. The superficial zone is taken as the region from the articular surface to ⅒ the distance to the calcified zone.

FIG. 2 shows that substantial chondrocyte death occurs in the superficial zone of articular cartilage when bathed in saline for about 24 and about 48 hours, respectively. The superficial zone is taken as the region from the articular surface to ⅒ the distance to the calcified zone. Chondrocyte death in the superficial zone is reduced in Ringer's Lactate at 24 hours but not at 48 hours. As above, full thickness discs (about 6 mm diameter) of articular cartilage from the bovine radial-carpal joint are immersed in various solutions for about 24 or about 48 hours, respectively, after which the cartilage is cut into 70 μm sections on a vibratome and stained with Syto 13 (Molecular Probes) and ethidium bromide to assess chondrocyte viability.

The results demonstrate the surprising and unexpected finding that chondrocyte death is substantially reduced at both 24 and 48 hours when the cartilage is bathed in the arthroguard adjuvant when compared to both saline and Ringer's Lactate solutions.

Example 4

Figure 6:
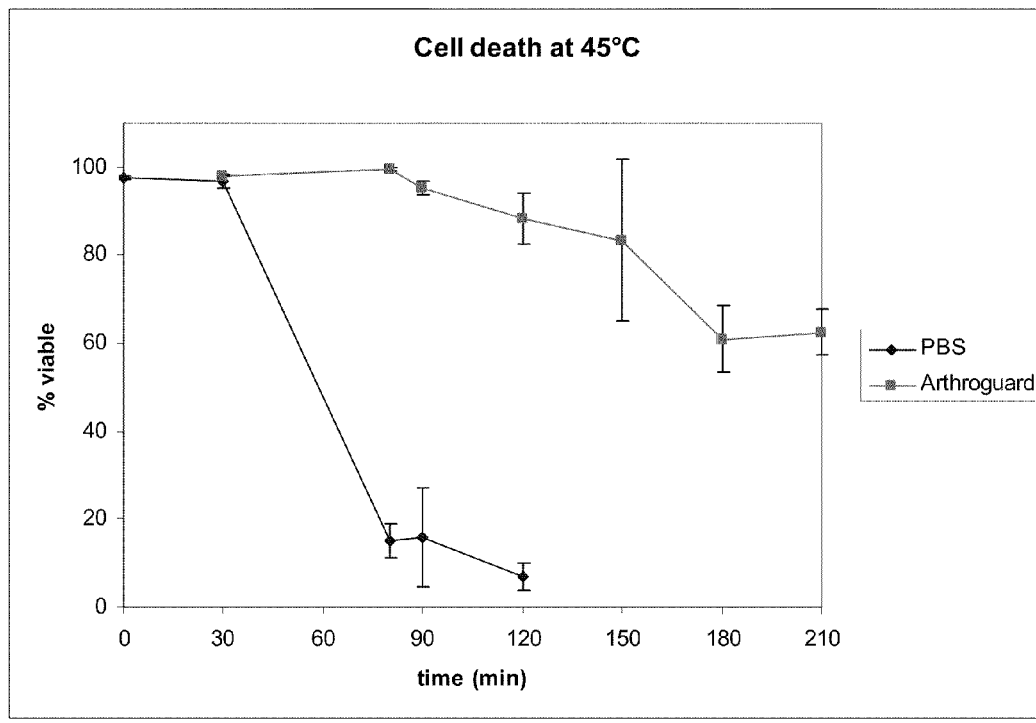
FIG. 6: Canine synovioctyes in suspension are immersed in either phosphate buffered saline (PBS) or arthroguard and are held at 45° C. for up to 2.5 hours. Cell viability is assessed using paravital dyes under ultraviolet illumination to indicate plasma membrane integrity. The figure shows the average percentage of viable cells in four separate fields (10× objective). The bars show the standard deviation of the mean.

FIG. 6 shows that substantial cell death occurs in a buffered, isotonic medium when incubated at 45° C. beginning at 30 minutes. This form of cell death is prevented when the cells are incubated in the arthroguard solution at the same temperature, for at least two hours.

This result demonstrates the surprising and unexpected finding that cell death due to exposure to high temperatures is substantially reduced when the cells are bathed in the arthroguard adjuvant when compared to phosphate buffered saline.

Example 5

Figure 7:
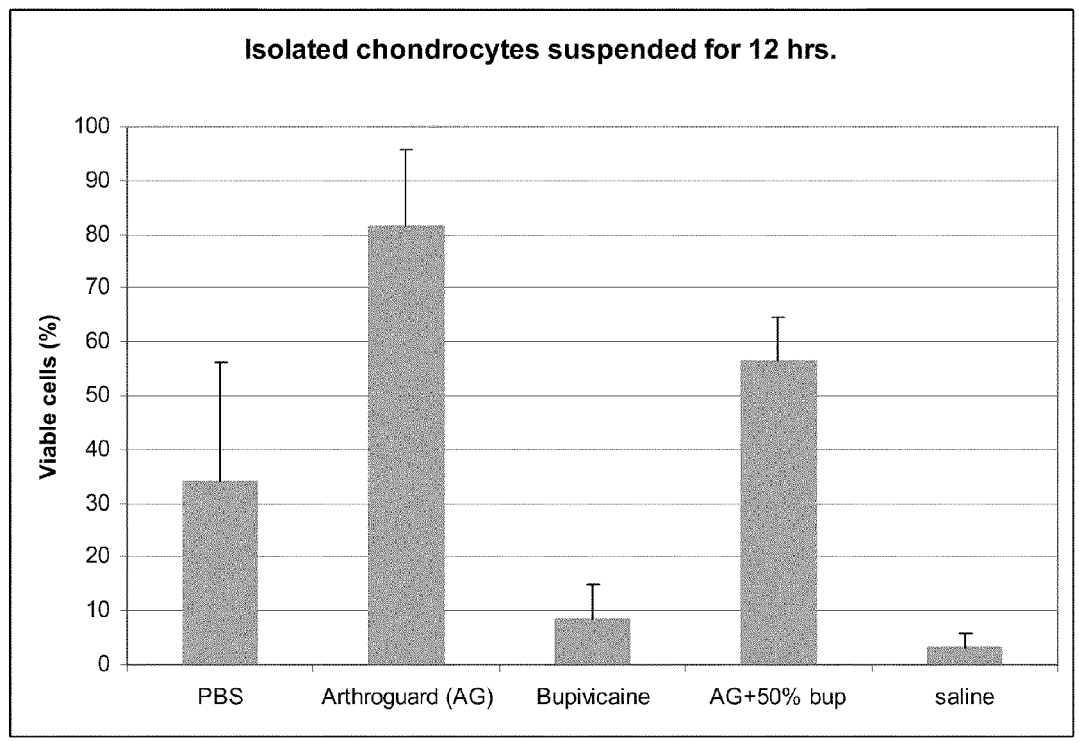
FIG. 7: Bovine chondrocytes suspended for 12 hrs. at 37° C. in various solutions of phosphate buffered saline (PBS), bupivacaine (1.25 mg/mL [0.125%]), arthroguard and saline. In these experiments, 2.5 mg/mL [0.25%] bupivacaine was combined with arthroguard to yield a final concentration of 1.25 mg/mL [0.125%] bupivacaine in arthroguard. for 12 hrs. Cell viability is assessed by membrane integrity dyes.

FIG. 7 shows that chondrocytes that have been isolated from the cartilage matrix lose viability when suspended in conventional irrigant solutions such as saline and phosphate buffered saline (PBS). The addition of the anaesthetic bupivicaine increases the amount of cell death. The addition of arthroguard allows the cells to maintain viability for the duration of the experiment (12 hrs) and substantially reduces the amount of cell death when the cells are exposed to bupivicaine.

This result demonstrates the surprising and unexpected finding that chondrocytes that have been isolated from the cartilage matrix are also protected by the arthroguard adjuvant from cell death caused by bupivicaine and by prolonged incubation in isotonic saline solutions.

Figure 3:
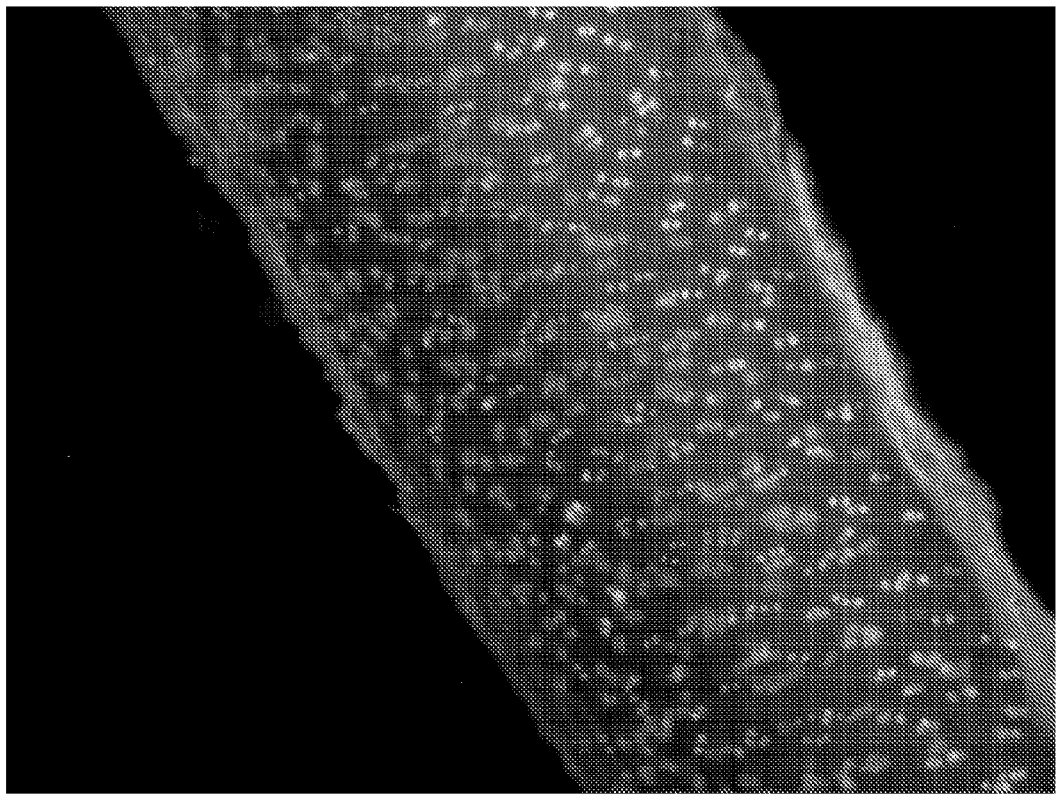
FIG. 3: Immunofluorescence microscopy showing the effects on cell viability of solutions containing bupivacaine (bupivacaine is supplied as a 2.5 mg/mL [0.25%] solution from the manufacturer). Full thickness discs of articular cartilage from the bovine radial-carpal joint were immersed in 1.25 mg/mL (0.125%) solutions of bupivacaine (diluted from 2.5/mg/mL to 1.25 mg/mL (0.25% to 0.125%) using phosphate buffered saline) for 24 hours, after which the cartilage is cut into 70 μm sections on a vibratome and stained with Syto 13 (Molecular Probes) and ethidium bromide to assess chondrocyte viability. Green fluorescence indicates live articular chondrocytes, red fluorescence indicates dead articular chondrocytes.
Figure 4:
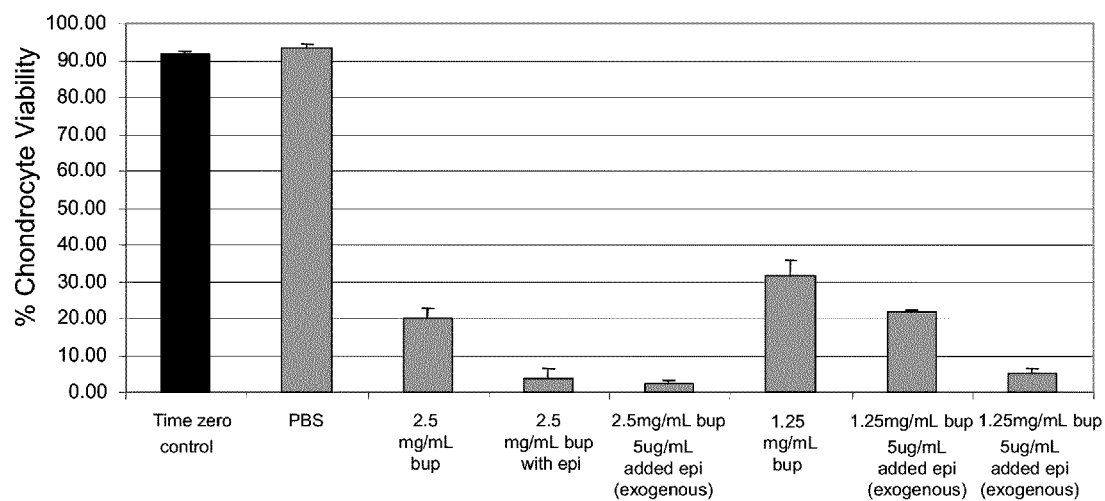
FIG. 4 demonstrates the effects on cell viability of solutions containing epinephrine and bupivacaine. Full thickness discs (6 mm diameter) of articular cartilage from the bovine radial-carpal joint were immersed in solutions of bupivacaine, bupivacaine with epinephrine (manufacturers solution), bupivacaine with exogenously added epinephrine (5 ug/mL final concentration). Bupivacaine concentrations (with or without epinephrine) for each solution were either 2.5/mg/mL [0.25%] or 1.25 mg/mL (0.25% to 0.125%) (diluted using phosphate buffered saline) for 24 hours, after which the cartilage is cut into 70 μm sections on a vibratome and stained with Syto 13 (Molecular Probes) and ethidium bromide to assess chondrocyte viability.
Figure 5:
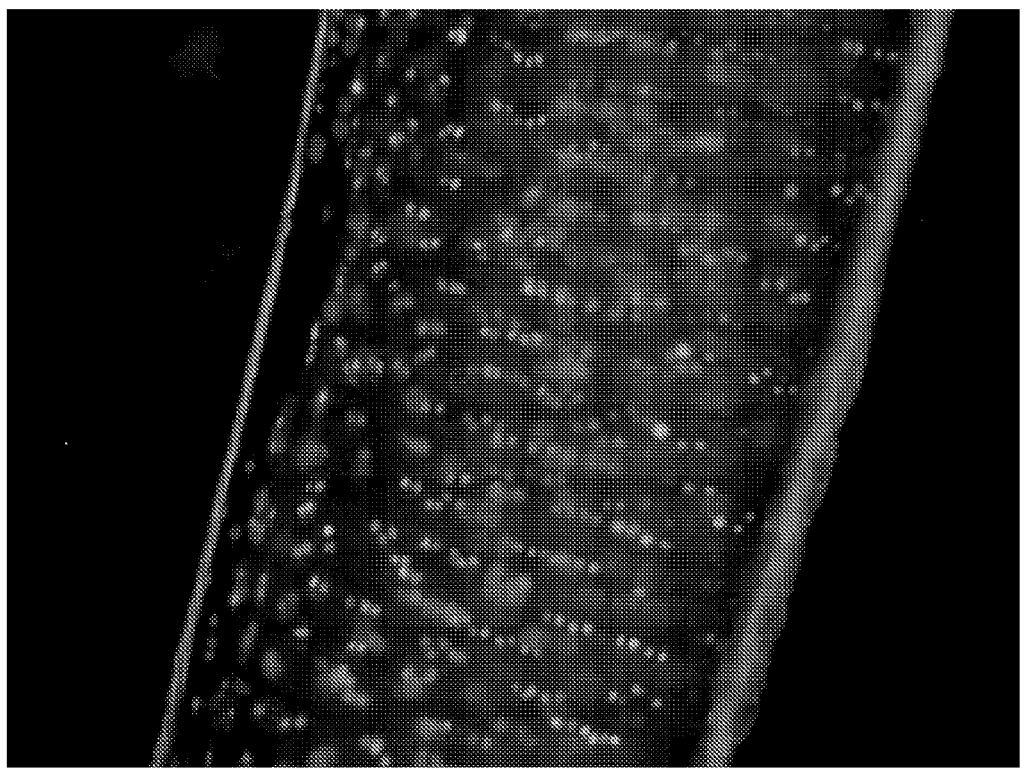
FIG. 5: Immunofluorescence microscopy showing the effects on cell viability of solutions containing bupivacaine (1.25 mg/mL [0.125%]) and arthroguard. In these experiments, 2.5 mg/mL [0.25%] bupivacaine was combined with arthroguard to yield a final concentration of 1.25 mg/mL [0.125%] bupivacaine in arthroguard. Green fluorescence indicates live articular chondrocytes, red fluorescence indicates dead articular chondrocytes.

FIG. 3 demonstrates the observed results attained using another exemplary embodiment of the present invention. In particular, the adjuvant composition additionally comprises epinephrine, and bupivicaine. When epinephrine is added to the solution of phosphate buffered saline with bupivicaine, chondrocyte death is approximately 53.5% at about 24 hours and approximately 97.5% at about 48 hours. On the other hand, when the cells are exposed to the arthroguard solution containing the same concentrations of epinephrine and bupivicaine, chondrocyte death is reduced to approximately 29% at about 24 hours and approximately 48% at about 48 hours.

Having described preferred embodiments of the invention with reference to the accompanying drawings, it is to be understood that the invention is not limited to the precise embodiments, and that various changes and modifications may be effected therein by those skilled in the art without departing from the scope or spirit of the invention as defined in the appended claims. Accordingly, the detailed description is to be taken in an illustrative, as opposed to a limiting sense.

What is claimed is:

1. A composition comprising isotonic phosphate buffered saline, a high molecular weight dextran, ascorbate, transferrin, and poloxamer surfactant P188.

2. The composition of claim 1, further comprising an anesthetic.

3. The composition of claim 2, wherein the anesthetic is a local anesthetic.

4. The composition of claim 2, wherein the anesthetic is selected from the group consisting of morphine, gabapentin, Opioids, Alfentanil, Anileridine, Fentanyl, Phenoperidine, Remifentanil, Sufentanil, Neuroactive steroids Alfaxalone, Minaxolone, Droperidol, Etomidate, Fospropofol, gamma-Hydroxybutyric acid, Ketamine/Esketamine, Midazolam, Propanidid, Propofol, and combinations thereof.

5. The composition of claim 3, wherein the local anesthetic is selected from the group consisting of bupivacaine, xylocaine/lidocaine, ropivacaine, and combinations thereof.

6. The composition of claim 1, further comprising epinephrine.

7. The composition of claim 1, further comprising an additional biocompatible solution.

8. A surgical adjuvant for ameliorating tissue or cellular damage comprising a combination of isotonic phosphate buffered saline, high molecular weight dextran, ascorbate, transferrin, and the poloxamer surfactant P188, wherein the adjuvant ameliorates or refuces tissue or cellular damage.

9. The surgical adjuvant of claim 8, wherein the tissue or cellular damage is due to a surgical procedure.

10. The surgical adjuvant of claim 8, wherein the adjuvant further comprises an anesthetic.

11. The surgical adjuvant of claim 10, wherein the anesthetic is a local anesthetic.

12. The surgical adjuvant of claim 10, wherein the anesthetic is selected from the group consisting of morphine, gabapentin, Opioids, Alfentanil, Anileridine, Fentanyl, Phenoperidine, Remifentanil, Sufentanil, Neuroactive steroids Alfaxalone, Minaxolone, Droperidol, Etomidate, Fospropofol, gamma-Hydroxybutyric acid, Ketamine/Esketamine, Midazolam, Propanidid, Propofol, and combinations thereof.

13. The surgical adjuvant of claim 11, wherein the local anesthetic is selected from the group consisting of bupivacaine, xylocaine/lidocaine, ropivacaine, and combinations thereof.

14. The surgical adjuvant of claim 8, further comprising epinephrine.

15. The surgical adjuvant of claim 8, further comprising an additional biocompatible solution.

16. The surgical adjuvant of claim 15, wherein the biocompatible solution comprises at least one of Ringer's solution, Ringer's Lactate, saline, balanced salt solutions, phosphate buffered saline, biopreservation solutions, Eurocollins solution, UW solution, Hank's buffered salt solution, Earl's balanced salt solution, Dulbecco's phosphate buffered saline or combinations thereof.

17. A method for ameliorating tissue or cellular damage in a patient due to an invasive procedure comprising administering to the patient an effective amount of the adjuvant of claim 8 before, during, and/or after a surgical procedure, wherein the adjuvant ameliorates tissue or cellular damage.

18. The method of claim 17, wherein the adjuvant further comprises an anesthetic.

19. The method of claim 17, wherein the adjuvant further comprises epinephrine.

20. The method of claim 17, wherein the procedure is an arthroscopic surgical procedure.

21. The method of claim 17, wherein the procedure is a minimally invasive endoscopic surgical procedure.

22. The method of claim 17, wherein the adjuvant composition is administered prior to the procedure.

23. The method of claim 17, wherein the adjuvant is administered during the procedure.

24. The method of claim 17, wherein the adjuvant is administered after the procedure.

25. The method of claim 17, wherein the adjuvant is administered at multiple times selected from the group consisting of before the procedure, during the procedure, after the procedure, and combinations thereof.

26. The method of claim 17, wherein the adjuvant is administered continuously during a portion of or throughout the entire procedure.

* * * * *